United States Patent
Strnad

(10) Patent No.: US 9,474,554 B2
(45) Date of Patent: Oct. 25, 2016

(54) SPINAL ROD CROSS CONNECTOR

(76) Inventor: Lee A. Strnad, Broadview Heights, OH (US)

(*) Notice: Subject to any disclaimer, the term of this patent is extended or adjusted under 35 U.S.C. 154(b) by 1345 days.

(21) Appl. No.: 12/247,510

(22) Filed: Oct. 8, 2008

(65) Prior Publication Data

US 2009/0105765 A1    Apr. 23, 2009

Related U.S. Application Data

(60) Provisional application No. 60/981,897, filed on Oct. 23, 2007.

(51) Int. Cl.
*A61B 17/70* (2006.01)

(52) U.S. Cl.
CPC ................................. *A61B 17/7049* (2013.01)

(58) Field of Classification Search
CPC .................. A61B 17/7049; A61B 17/7052
USPC ................... 606/250, 251, 252, 253, 278
See application file for complete search history.

(56) References Cited

U.S. PATENT DOCUMENTS

| | | |
|---|---|---|
| 5,084,049 A | 1/1992 | Asher et al. |
| 5,330,473 A | 7/1994 | Howland |
| 5,669,910 A | 9/1997 | Korhonen et al. |
| 5,980,521 A | 11/1999 | Montague et al. |
| 6,113,600 A | 9/2000 | Drummond et al. |
| 6,136,003 A | 10/2000 | Hoeck et al. |
| 6,217,578 B1 | 4/2001 | Crozet et al. |
| 6,413,258 B1 | 7/2002 | Bernhardt, Jr. |
| 6,524,310 B1 | 2/2003 | Lombardo et al. |
| 6,554,832 B2 | 4/2003 | Shluzas |
| 6,616,668 B2 | 9/2003 | Altarac et al. |
| 6,783,526 B1 | 8/2004 | Lin et al. |
| 6,875,211 B2 | 4/2005 | Nichols et al. |
| 6,960,212 B2 * | 11/2005 | Richelsoph et al. .......... 403/342 |
| 7,066,938 B2 | 6/2006 | Slivka et al. |
| 7,122,036 B2 | 10/2006 | Vanacker |
| 7,806,912 B2 * | 10/2010 | Lawton .............. A61B 17/7049 606/250 |
| 7,837,714 B2 * | 11/2010 | Drewry et al. ............... 606/250 |
| 2004/0133203 A1 * | 7/2004 | Young et al. .................. 606/61 |
| 2005/0107789 A1 * | 5/2005 | Sweeney ............ A61B 17/7052 606/86 A |
| 2005/0228377 A1 * | 10/2005 | Chao .................. A61B 17/7052 606/252 |
| 2006/0058789 A1 | 3/2006 | Kim et al. |
| 2007/0161988 A1 | 7/2007 | Drewry et al. |
| 2007/0219552 A1 | 9/2007 | Zucherman et al. |
| 2008/0082112 A1 * | 4/2008 | Lawton et al. ............... 606/151 |
| 2008/0172093 A1 * | 7/2008 | Nilsson ......................... 606/250 |

* cited by examiner

*Primary Examiner* — Ellen C Hammond
*Assistant Examiner* — Christina Negrellirodrique
(74) *Attorney, Agent, or Firm* — Tarolli, Sundheim, Covell & Tummino LLP

(57) ABSTRACT

A cross connector assembly is provided. In one embodiment, the cross connector is configured to engage a pair of rods in a spinal implant assembly. In an exemplary embodiment, the cross connector assembly includes at least one elongated top member having a pair of hooked-shaped ends and a pair of sliding members configured to slideably engage the at least one elongated top member. The cross connector may further include an upper fastener and a lower fastener engaged with the upper fastener configured to translate upon rotation of the upper fastener and engage the sliding members, biasing them from a first position to a second position.

17 Claims, 11 Drawing Sheets

SPINAL ROD CROSS CONNECTOR

CROSS REFERENCE TO RELATED APPLICATIONS

This application claims the benefit of priority of U.S. Provisional Application No. 60/981,897, filed on Oct. 23, 2007.

FIELD OF INVENTION

The present application relates to spinal fixation devices. More particularly, the present application relates to cross connectors for spinal fixation elements, such as rods, configured to be implanted in a patient's spinal system.

BACKGROUND

Spinal fixation devices are used in orthopedic surgery to align or repair a relationship between vertebrae. Such devices may include one or more rods that are attached to vertebrae by screws, bolts, hooks, or other anchoring devices. The rods may have a contour that is pre-formed according to the properties of the implantation site. Alternatively, the contour of the rods may be created during surgery to conform to the implantation site. The rods hold the vertebrae in a desired spatial relationship until healing or spinal fusion has taken place, or for some other desired period of time.

In cases where multiple rods are used, cross connectors may be used to provide additional stability and maintain the rods in a desired position. One known type of cross connector is a rod having clamps formed on opposite ends for mating with spinal rods. Typically, such a cross connector employs two set screws, or other such locking mechanisms to fix each end of the cross connector to the spinal rods. Telescopic and other length adjustable cross connectors are also known, which may include a third set screw or other locking mechanism to fix the length of the cross connector.

U.S. Pat. No. 5,330,473 discloses a cross connector that employs a single bolt. The cross connector includes a lower saddle and an upper saddle. The lower saddle includes arcuate channels to receive spinal rods. The upper saddle is configured to mate with the lower saddle and define upper portions of the arcuate channels. The upper channel is locked in place with the bolt.

U.S. Patent Application Publication 2006/0058789 discloses a cross connector that employs a single locking mechanism. When the locking mechanism is tightened, it engages sliding or pivoting "shoes" which lock the cross connector in place with respect to a pair of spinal rods.

BRIEF DESCRIPTION OF THE DRAWINGS

In the accompanying drawings, structures are illustrated that, together with the detailed description provided below, describe exemplary embodiments of the claimed invention.

In the drawings and description that follows, like elements are identified with the same reference numerals. The drawings are not to scale and the proportion of certain elements may be exaggerated for the purpose of illustration.

DETAILED DESCRIPTION

Figure 1:
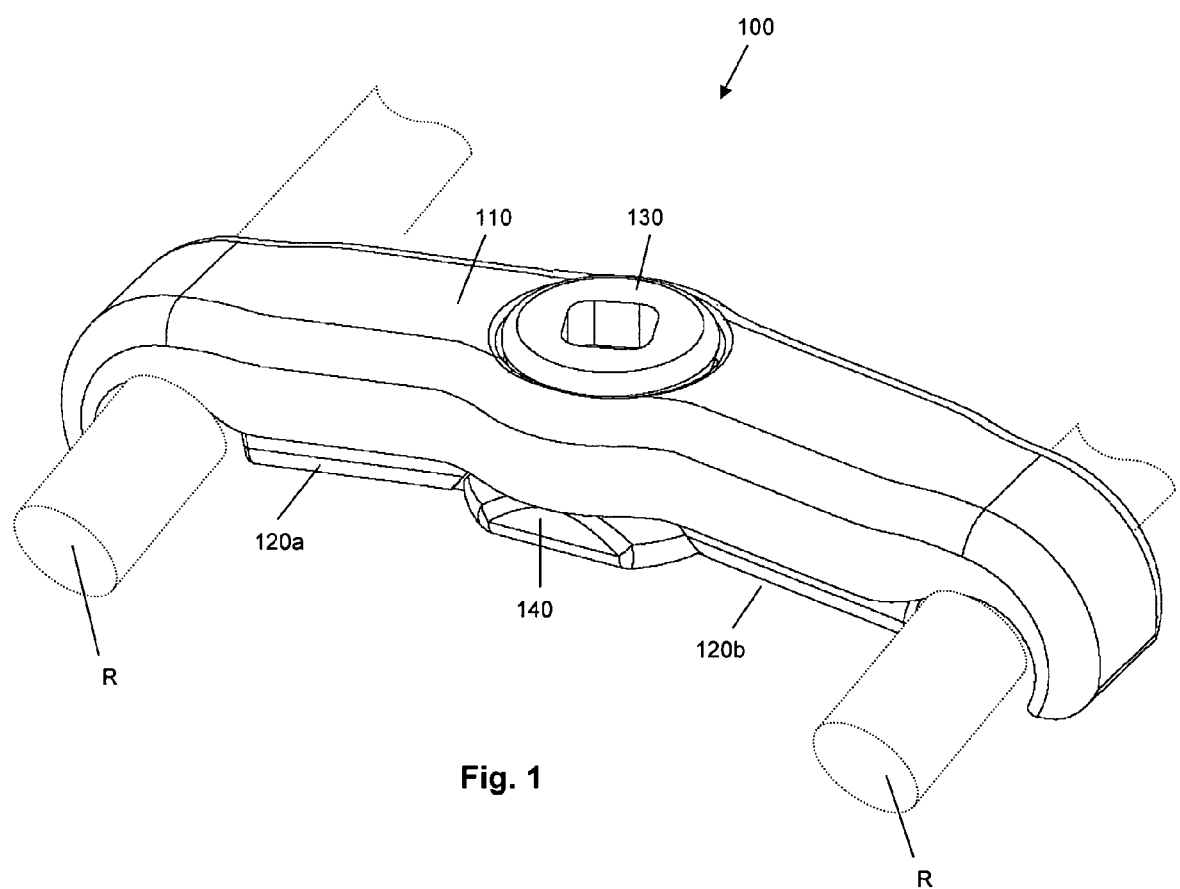
FIG. 1 is a perspective view of one embodiment of a cross connector assembly and a pair of spinal rods.

FIGS. 1-5 illustrate one embodiment of a cross connector assembly 100 for a pair of spinal rods R in a spinal fixation assembly. FIG. 1 illustrates a perspective view of the cross connector assembly 100. The cross connector assembly 100 includes an elongated top member 110 having first and second rod receiving portions, such as hooked-shaped ends that form a pocket configured to receive the spinal rods R.

In the illustrated embodiment, the cross connector assembly 100 includes a first sliding member 120a and a second sliding member 120b. Each of the first and second sliding members 120a,b is configured to engage spinal rods R. The cross connector assembly further includes an upper fastener 130. In the illustrated embodiment, the upper fastener 130 is a threaded flat-head bolt with a square aperture for receiving a tool, such as a screwdriver, Allen wrench, or other known tool. This aperture may be referred to as a square (or Robertson) drive design. In alternative embodiments (not shown), the upper fastener may have a pan head, a button head, a round head, a truss head, an oval head, a bugle head, a cheese head, a fillister head, a socket head, a mirror screw head, or other known head. In another alternative embodiment (not shown), the upper fastener may be headless. In other alternative embodiments (not shown), the upper fastener may have a flathead, cross head, cross point, cruciform, Phillips, Pozidriv, torx, hex, tri-wing, torq-set, spanner head, or other known drive design. In another alternative embodiment, the upper fastener may be configured to be rotated by hand. In other alternative embodiments (not shown), the upper fastener may be a screw, a pinned shaft, or other known fastener.

With continued reference to FIG. 1, the cross connector assembly 100 further includes a lower fastener 140. Together, the upper fastener 130 and the lower fastener 140 form a locking mechanism. In the illustrated embodiment, the lower fastener is a nut with threaded aperture corresponding to the threads of the upper fastener 130. The lower fastener 140 has a pair of angled sides configured to engage the first and second sliding members 120a,b. In one known embodiment, the lower fastener 140 has conical sides. In another known embodiment, the lower fastener 140 has spherical sides. The lower fastener 140, alone or in combination with the upper fastener 140, may also be referred to as an engagement member.

In one embodiment, the components of the cross connector assembly 100 are all constructed of the same material. Exemplary materials include TI-6AL-4V titanium or 316 stainless steel. However, it should be understood that any approved implant grade material could be used. In an alternative embodiment, the components may be made of different materials.

Figure 2:
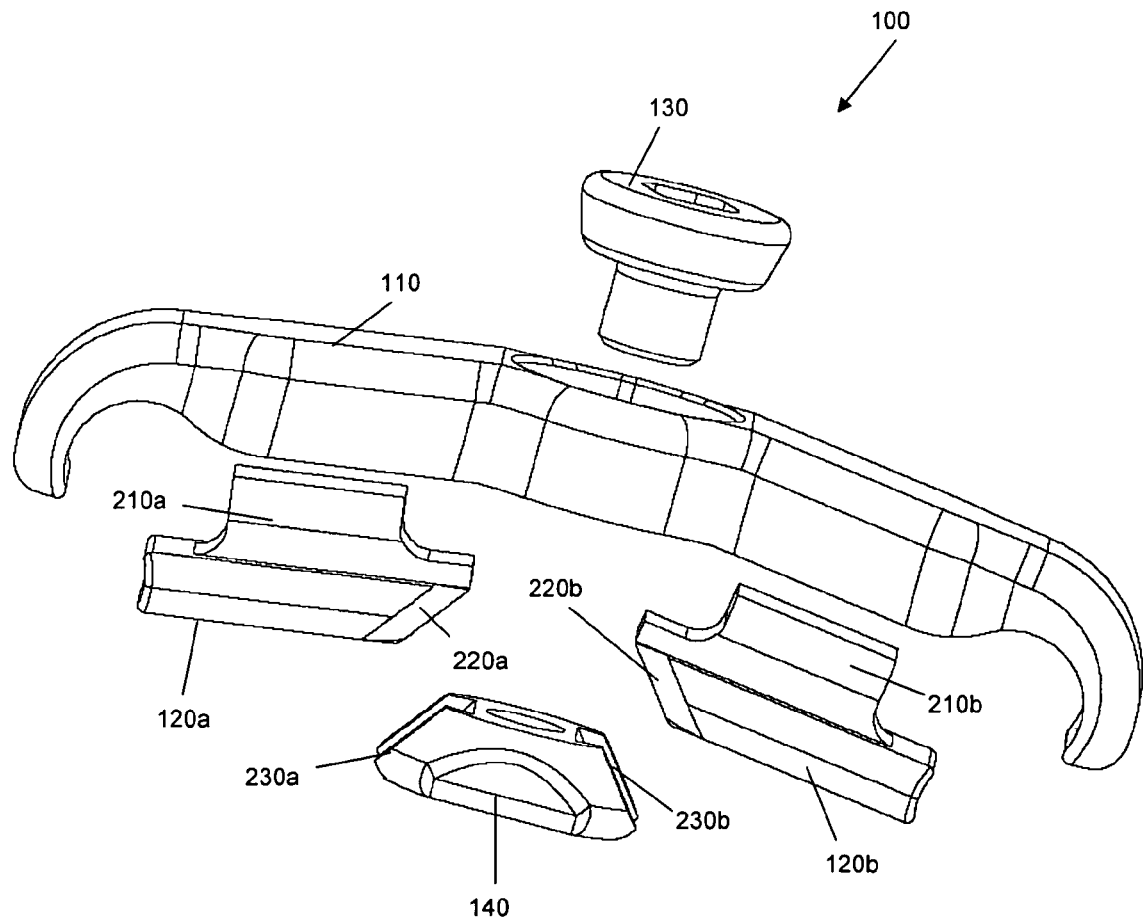
FIG. 2 is an exploded perspective view of the cross connector assembly.

FIG. 2 illustrates an exploded perspective view of the cross connector assembly 100, further illustrating the components of the cross connector assembly 100. As can be seen in the illustrated embodiment, the first and second sliding members 120a,b each include upper portions 210a,b configured to slideably engage channels in the bottom surface of the elongated top member 110. The upper portions 210a,b and the channels may have various corresponding profiles, as illustrated in FIGS. 3A-B.

Figure 3A:
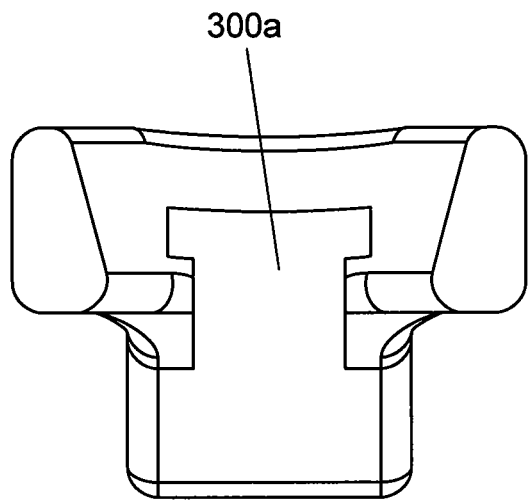
FIGS. 3A-C are cross-sections of alternative embodiments of channels employed in a top member of a cross connector assembly.
Figure 3B:
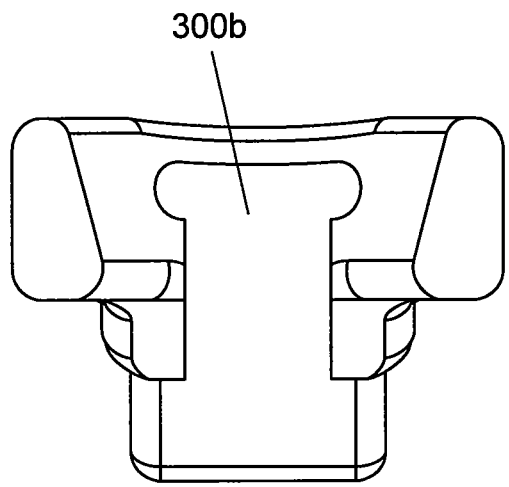
Figure 3C:
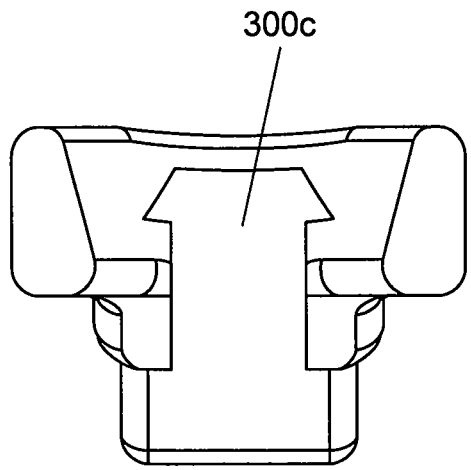

FIG. 3A illustrates a cross section of an elongated top member having a T-shaped channel 300a. FIG. 3B illustrates a cross section of an elongated top member having a round channel 300b. FIG. 3C illustrates a cross section of an elongated top member having a dove-tailed channel 300c. However, it should be understood that the channel may have any other geometric profile. It should be further understood that the upper portions 210a,b of the sliding members 120a,b may have a shape corresponding to the shape of the channel. In alternative embodiments (not shown), the sliding members 120a,b may include rollers, ball bearings, or other such devices along the upper portions 210a,b to facilitate translation along the grooves or channels in the elongated top member 110.

Returning now to FIG. 2, the first and second sliding members 120a,b each include a corresponding angled projection 220a,b configured to mate with corresponding first and second grooves 230a,b in the lower fastener 140. In one embodiment, the first and second grooves 230a,b in the lower fastener 140 have profiles corresponding to the shape of the angled projections 220a,b. In the illustrated embodiment, the first and second angled projections 220a,b have angled sidewalls, and the first and second grooves 230a,b have corresponding angles to retain the first and second sliding members 120a,b and maintain them in a desired location. In an alternative embodiment, the first and second grooves 230a,b in the lower fastener 140 are wider than the angled projections 220a,b. In another alternative embodiment (not shown), the lower fastener 140 does not include grooves, and the angled sides of the lower fastener are in contact with the angled projections 220a,b of the lower fastener 140.

In other alternative embodiments, the angled projections 220a,b have a spherical or conical profile. In still other alternative embodiments, the angled projections 220a,b may have any geometric profile. In additional alternative embodiments, the sliding members 120a,b may include rollers, ball bearings, or other such devices to facilitate translation along the lower fastener 140.

Figure 4A:
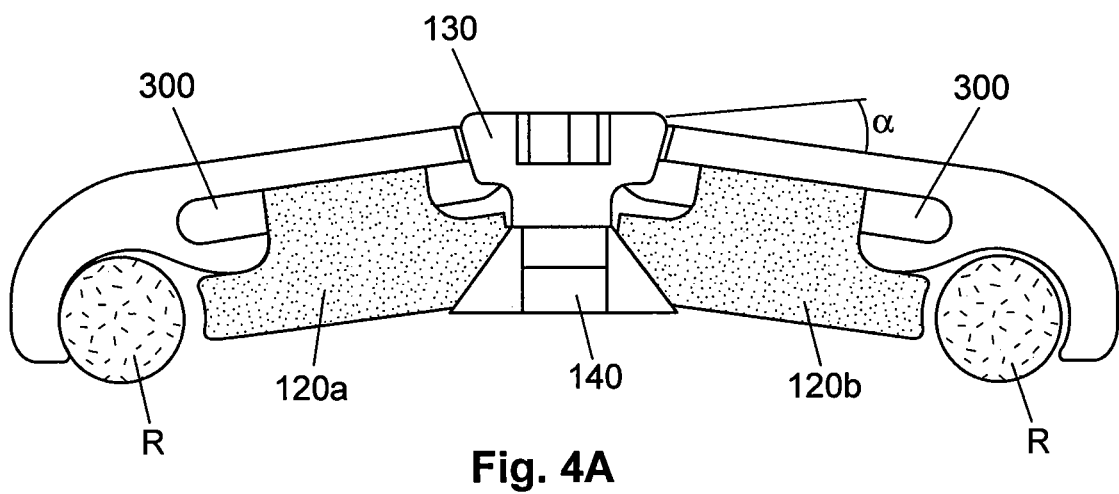
FIG. 4A is a front cross-section of the cross connector assembly in an open position.
Figure 4B:
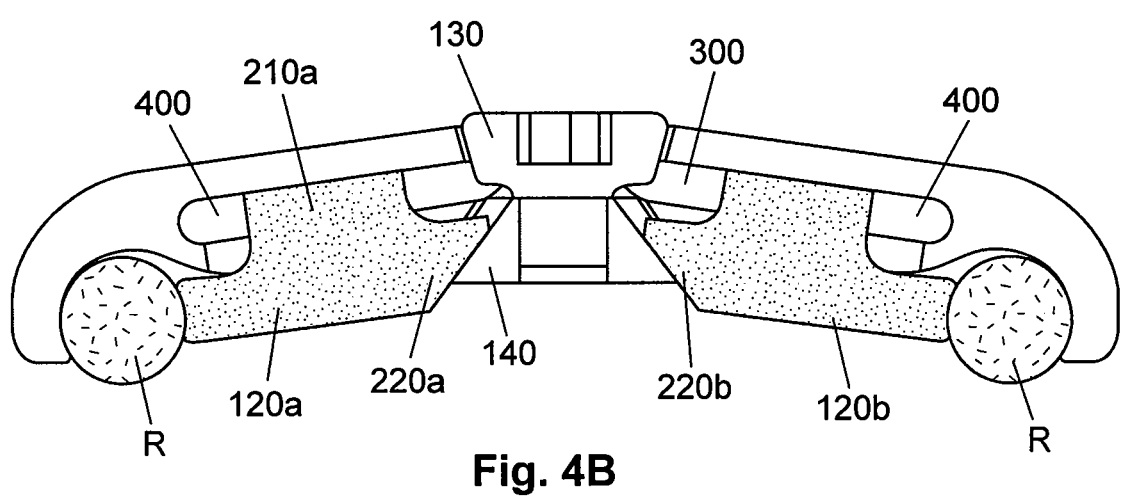
FIG. 4B is a front cross-section of the cross connector assembly in a closed position.

FIGS. 4A and 4B illustrate front cross-sections of the cross-connector assembly 100. In the illustrated embodiment, the upper surface of the elongated top member 110 has a slope α in the longitudinal direction toward the center to provide additional space for the dura, bony anatomy, and fusion mass. In one embodiment, the upper surface of the elongated top member 110 has a slope α of between about 10° to about 15°. In an alternative embodiment, the upper surface of the elongated top member 110 may have a slope α of between about 5° to about 30°. In another alternative embodiment, the upper surface of the elongated top member 110 may have a slope α of between about 0° to about 45°. In alternative embodiments (not shown), the elongated top member 110 has a flat upper surface to minimize the profile of the cross connector assembly 100.

In FIG. 4A, the cross-connector assembly 100 is in an open position such that the hooked-shaped ends of the elongated top member 110 may be placed over a pair of spinal rods R. After the cross-connector assembly 100 is in place, a user may rotate the upper fastener 130 by hand or with an appropriate tool. As the upper fastener 130 is rotated, its threads mesh with the threaded aperture of the lower fastener 140, causing the lower fastener 140 to move upwards, as shown in FIG. 3B. As the lower fastener 140 moves upwards, the angled portions 220a,b of the first and second sliding members 120a,b slide along the grooves 230a,b of the lower fastener 140 and the upper portions 210a,b of the first and second sliding members 120a,b slide along the channels 300 of the elongated top member 110. The user may continue to rotate the upper fastener 130 until the sliding members 120,b contact the rods R and sufficient pressure is applied to lock the cross connector assembly 100 in place. In other words, the cross connector assembly 100 may be locked in place by tightening a single fastener. In the illustrated embodiment, the channels 300 include rounded ends 400 that function as stops for the sliding members 120a,b to prevent the sliding members 120a,b from sliding out of the channels 300 when spinal rods are not present. In alternative embodiments, other shapes may be employed for the stops.

Figure 5:
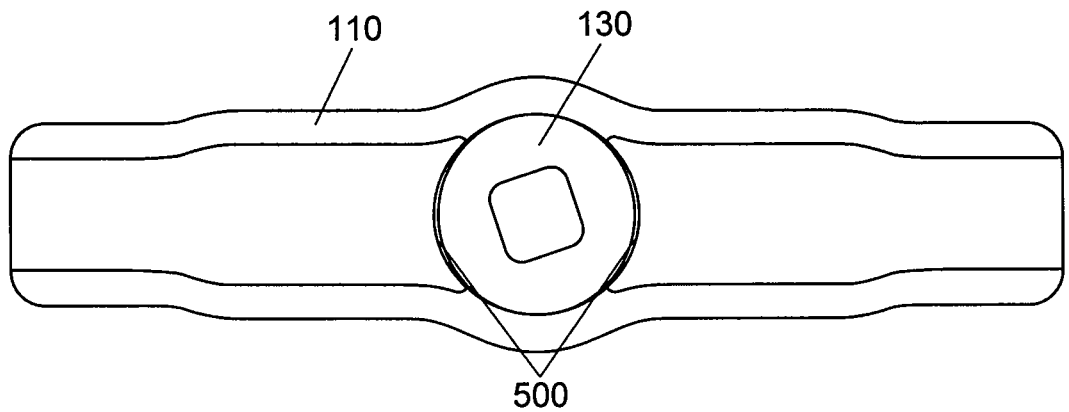
FIG. 5 is a top view of the cross connector assembly.
Figure 6:
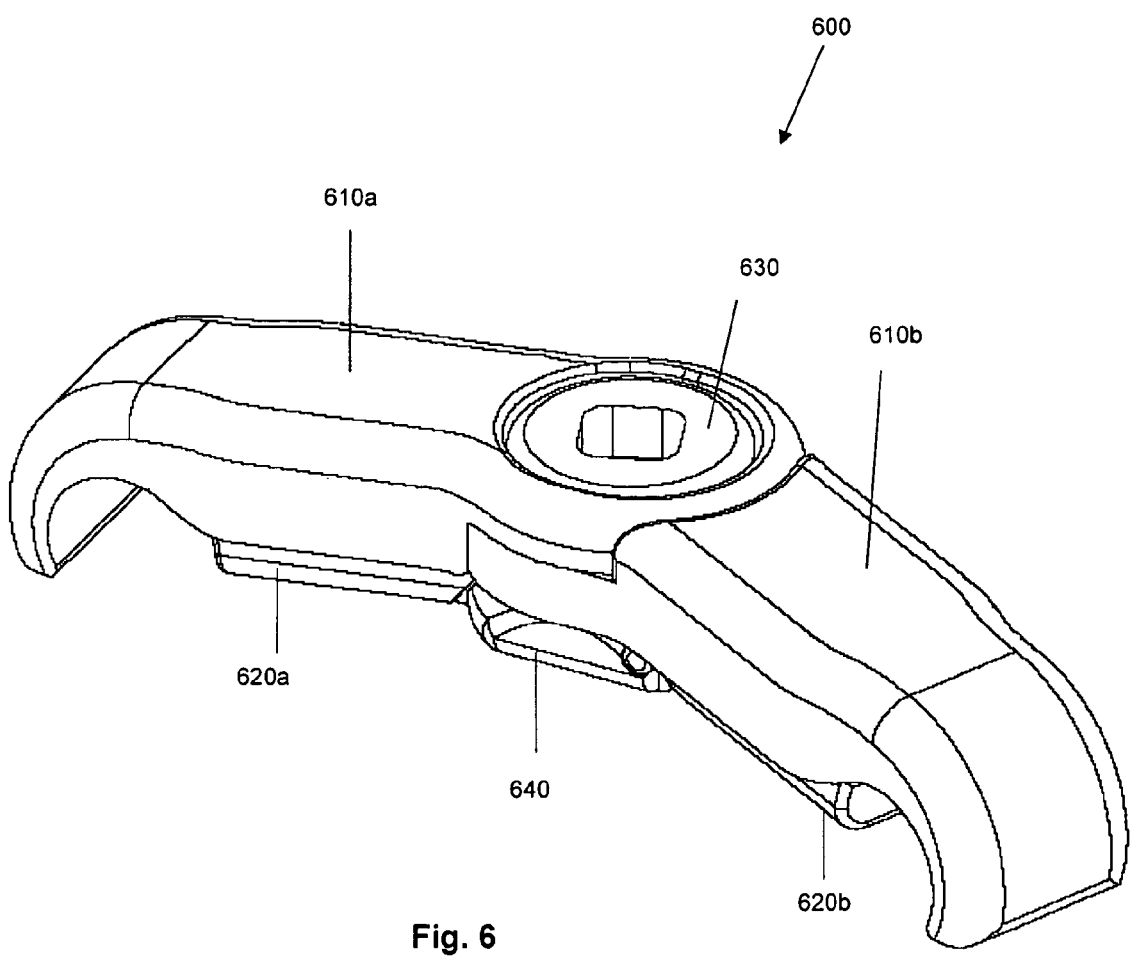
FIG. 6 is a perspective view of a second embodiment of a cross connector assembly.

FIG. 5 illustrates a top view of the cross connector assembly 100. As can be seen in the illustrated embodiment, the upper fastener 130 is housed in an aperture 500 of the elongated top member 110. In the illustrated embodiment, the aperture 500 is oblong, or oval shaped, and the head of the upper fastener 130 is circular. This configuration will create gaps between the left and/or right portions of the upper fastener 130 and the elongated top member 110. The gap will aid in the assembling of the components of the cross connector assembly 100 by compensating for any differences or tolerance stack ups in the components. In an alternative embodiment (not shown), the aperture 500 may be circular, having a diameter larger than the diameter of the head of the upper fastener 130. In another alternative embodiment (not shown), the aperture 500 may be circular, with the same diameter as the diameter of the head of the upper fastener 130.

The cross connector assembly 100, illustrated in FIGS. 1-5, does not have an adjustable length, and is configured to be employed with a pair of spinal rods that are spaced apart by a predetermined distance corresponding to the length of the cross connector assembly 100. In this embodiment, cross connector assemblies of different lengths may be made to accommodate a variety of spinal rod spacings.

FIGS. 6-9 illustrate an alternative embodiment of a cross connector assembly 600. In the illustrated embodiment, the cross connector assembly 600 is adjustable to accommodate a range of spinal rod spacings. The cross connector assembly 600 includes a first elongated top member 610a pivotally connected to a second elongated top member 610b. Each of the first and second elongated top members 610a,b has a hooked-shaped end forming a pocket configured to receive spinal rods or other rod receiving portion. In the illustrated embodiment, the upper surface of the first and second elongated top members 610a,b may be curved or angled toward the center of the cross connector assembly 600 to provide additional space for the dura, bony anatomy, and fusion mass. In one embodiment, the upper surface of the elongated top members 610a,b may have an angle between about 10° to about 15°. In an alternative embodiment, the upper surface of the elongated top members 610a,b may have an angle between about 5° to about 30°. In another alternative embodiment, the upper surface of the elongated top members 610a,b may have an angle between about 0° to about 45°. In alternative embodiments (not shown), the first and second elongated top members 610a,b each have a flat upper surface to minimize the profile of the cross connector assembly 600.

In the illustrated embodiment, the cross connector assembly 600 further includes first and second sliding members 620a,b, and an engagement member including an upper fastener 630 and a lower fastener 640. These components are substantially the same as the first and second sliding members 120a,b, upper fastener 130, and lower fastener of the cross connector assembly 100 described above with reference to FIGS. 1-5, except for the additional features that will be described below.

Figure 7:
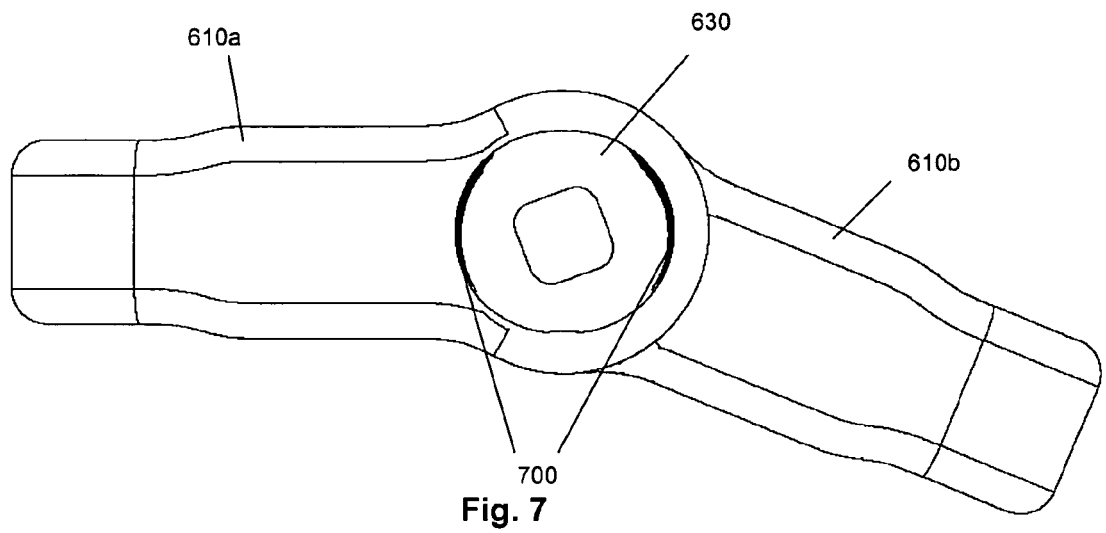
FIG. 7 is a top view of the second embodiment of the cross connector assembly.

FIG. 7 illustrates a top view of the cross connector assembly 600. In the illustrated embodiment, the first and second elongated top members 610a,b are pivotally connected at a central portion of the cross connector assembly 600, about an aperture 700 for receiving the upper fastener 630. In the illustrated embodiment, the first elongated top member 610a is positioned at an angle with respect to the second elongated top member 610b. In one embodiment, the second elongated top member 610b is configured to pivot smoothly and may be pivoted within a range of about −20° to about 20° with respect to the first elongated top member 610a. In an alternative embodiment, the second elongated top member 610b is configured to pivot smoothly and may be pivoted within a range of about −45° to about 45° with respect to the first elongated top member 610a. In yet another alternative embodiment, the second elongated top member 610b may be configured to be pivoted to any desired angle with respect to the first elongated top member 610a.

In an alternative embodiment, the pivotal connection between the first and second elongated top members 610a,b is ratcheted or otherwise configured such that the elongated top members 610a,b may be positioned among a finite number of detent positions. This may be accomplished by knurling the components, or forming teeth or serrations on the components, or by using other known methods to create detent positions.

With continued reference to FIG. 7, the aperture 700 formed by the first and second elongated top members 610a,b is oblong, or oval shaped and the head of the upper fastener 630 is circular, similar to the configuration of the cross connector assembly 100 illustrated in FIG. 5. In an alternative embodiment (not shown), the aperture 700 may be circular, having a diameter larger than the diameter of the head of the upper fastener 630. In another alternative embodiment (not shown), the aperture 700 may be circular, with the same diameter as the diameter of the head of the upper fastener 630.

Figure 8:
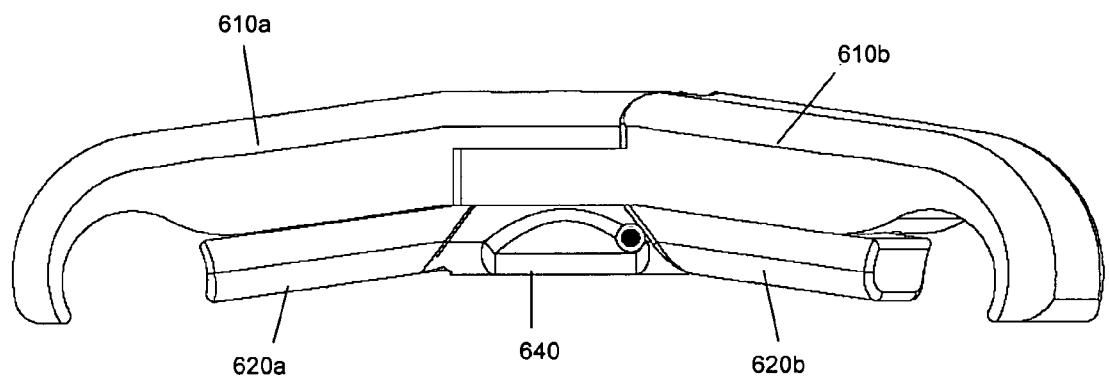
FIG. 8 is a front view of the second embodiment of the cross connector assembly.

FIG. 8 illustrates a front view of the cross connector assembly 600. In the illustrated embodiment, the first sliding member 620a includes an angled portion configured to mate with a groove in the lower fastener 640 in a fashion similar to that described above with reference to cross connector assembly 100. In this embodiment, the second sliding member 620b has a profile corresponding to the curved side of the lower fastener 640 which allows it to slide along the lower fastener 640 as the first and second elongated top member 610a,b are pivoted. This relationship is shown in further detail in the close up perspective view of the lower fastener 640 and the second sliding member 620b illustrated in FIG. 9.

Figure 9:
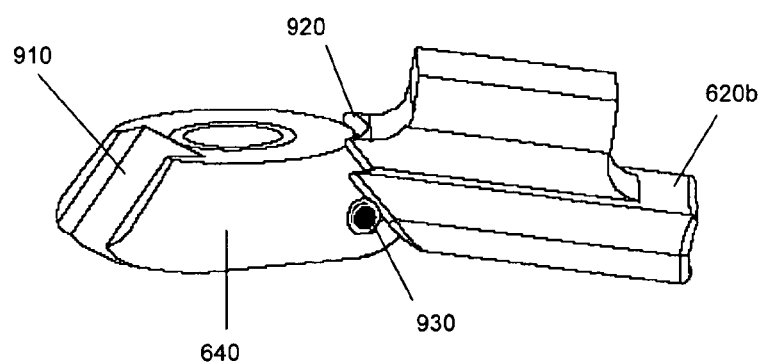
FIG. 9 is a close up perspective view of a fastener and a sliding member of the second embodiment of the cross connector assembly.

As shown in FIG. 9, in one embodiment, the lower fastener 640 includes a single groove 910 in an otherwise conically shaped surface. In an alternative embodiment (not shown), the lower fastener 640 has a substantially spherical surface.

In the illustrated embodiment, the second sliding member 620b includes an arcuate end 920 configured to mate with the curved surface of the lower fastener 640. In alternative embodiments (not shown), the second sliding member 620b may have a straight or rounded end, or an end having any known geometric profile. In other alternative embodiments (not shown), the second sliding member 620b may include rollers, ball bearings, or other devices to aid in the slidable engagement.

With continued reference to FIG. 9, the lower fastener 640 further includes a stop 930. In the illustrated embodiment, the stop 930 is a dowel pin that is press fit into a bore of the lower fastener 640. In an alternative embodiment (not shown), the stop is one or more threaded members, such as a screw, a bolt, a headless threaded rod, or any other threaded member. In another alternative embodiment (not shown), the stop is a protrusion that is machined into the lower fastener 640. In yet another alternative embodiment (not shown), the stop is a member that is affixed to the lower fastener 640 via a known affixing means, such as welding, brazing, or the use of adhesive.

In one embodiment, the stop 930 protrudes from two sides of the lower fastener 640, thereby forming a first and second boundary defining a range through which the second elongated top member 610b and second sliding member 620b may be pivoted. In an alternative embodiment (not shown), a stop may be employed on one of the first and second elongated top members 610a,b in lieu of the stop 930 on the lower fastener 640.

Figure 10:
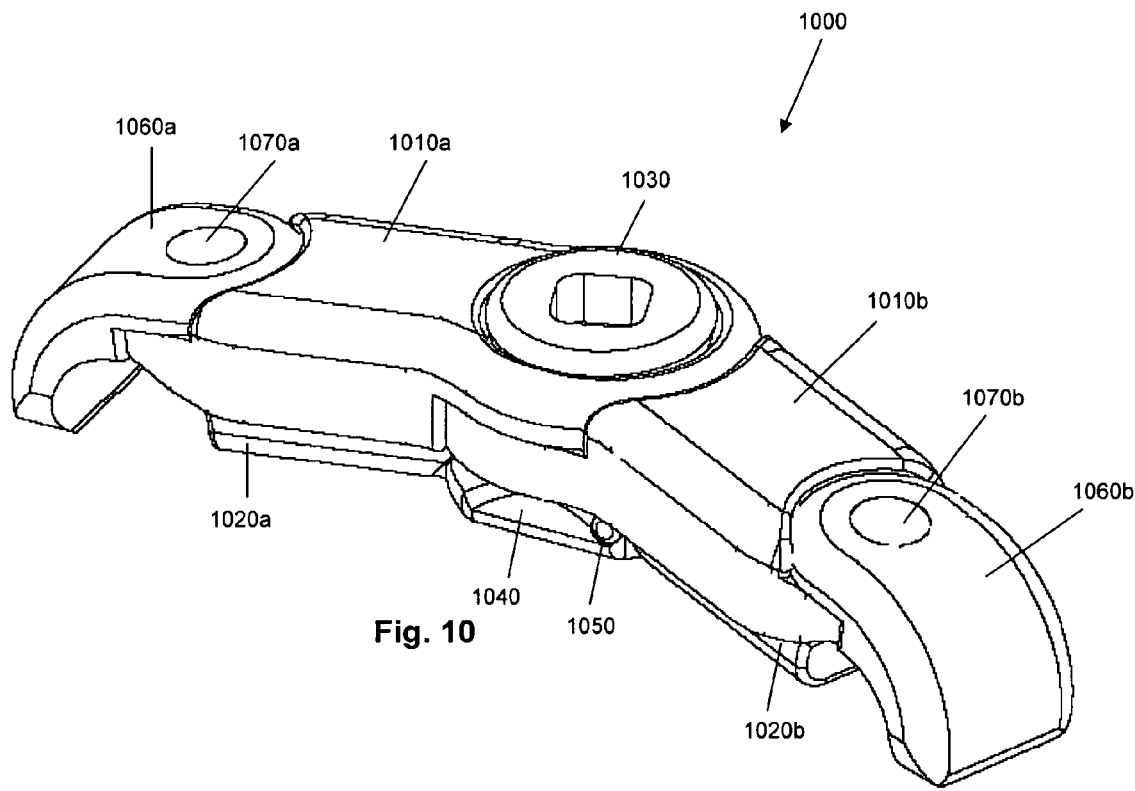
FIG. 10 is a perspective view of a third embodiment of a cross connector assembly.
Figure 11:
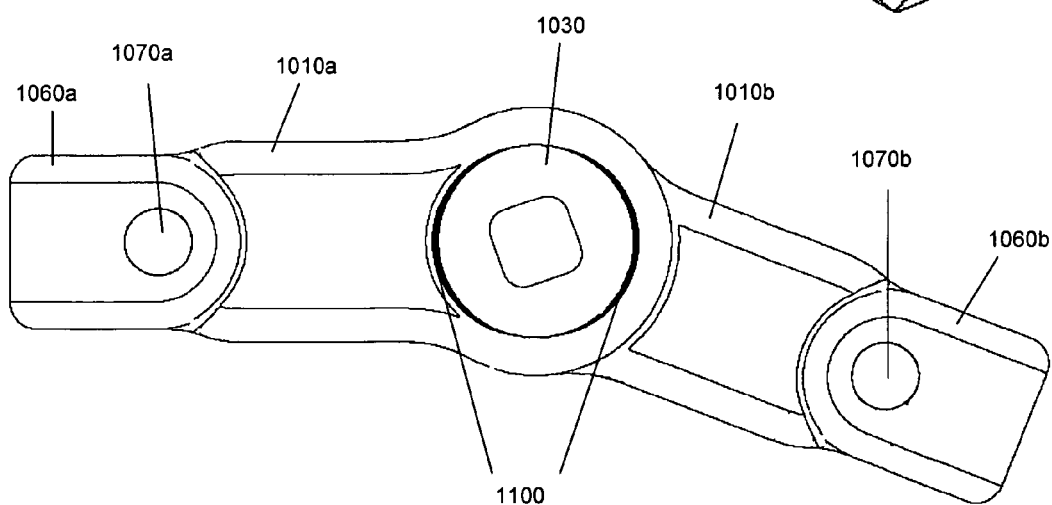
FIG. 11 is a top view of the third embodiment of the cross connector assembly.

FIGS. 10-11 illustrate another alternative embodiment of a cross connector assembly 1000. The cross connector assembly 1000 is substantially the same as the adjustable cross connector assembly 600 illustrated in FIGS. 6-9, except it includes first and second pivotal fingers 1060a,b, each forming a pocket configured to receive a spinal rod. The cross connector assembly 1000 includes first and second elongated top members 1010a,b, first and second sliding members 1020a,b, and a locking mechanism including an upper fastener 1030, and a lower fastener 1040 with a stop 1050. The lower fastener 1040, alone or in combination with the upper fastener 1030, may also be referred to as an engagement member. These components are substantially the same as the corresponding first and second elongated top members 610a,b, first and second sliding members 620a,b, upper fastener 630, and lower fastener 640 with stop 930 of the cross connect assembly 600 illustrated in FIGS. 6-9.

In the illustrated embodiment, the cross connector assembly 1000 includes first and second pivotal fingers 1060a,b configured to pivot about first and second pivot axes 1070a, b. In one embodiment, the first and second pivotal fingers 1060a,b are configured to pivot smoothly and may be pivoted to any desired angle within the boundary defined by the stop 1050. In an alternative embodiment, the first and second pivotal axes 1070a,b are ratcheted or otherwise configured such that the elongated top members 610a,b may be positioned among a finite number of detent positions.

In the illustrated embodiment, the angle between the first and second elongated top members 1010a,b may be pivotally adjusted as desired to accommodate spinal rods having a range of spacings. Further, the pivotal fingers 1060a,b may also be pivotally adjusted to create an improved fit around the spinal rods, or to accommodate a pair of spinal rods that are oriented in a non-parallel alignment.

FIG. 11 illustrates a top view of the cross connector assembly 1000. In the illustrated embodiment, the first and second elongated top members 1010a,b are pivotally connected at a central portion of the cross connector assembly 600, about an aperture 1100 for receiving the upper fastener 1030. The first and second elongated top members 1010a,b may be configured to pivot smoothly or otherwise configured such that the elongated top members 1010a,b may be positioned among a finite number of detent positions. This may be accomplished by knurling the components, or forming teeth or serrations on the components, or by using other known methods to create detent positions.

With continued reference to FIG. 11, the aperture 1100 formed by the first and second elongated top members 1010a,b is oblong, or oval shaped, and the head of the upper fastener 1030 is circular similar to the configuration of the cross connector assembly 100 illustrated in FIG. 5. In an alternative embodiment (not shown), the aperture 1100 may be circular, having a diameter larger than the diameter of the head of the upper fastener 1030. In another alternative embodiment (not shown), the aperture 1100 may be circular, having the same diameter as the diameter of the head of the upper fastener 1030.

Figure 12:
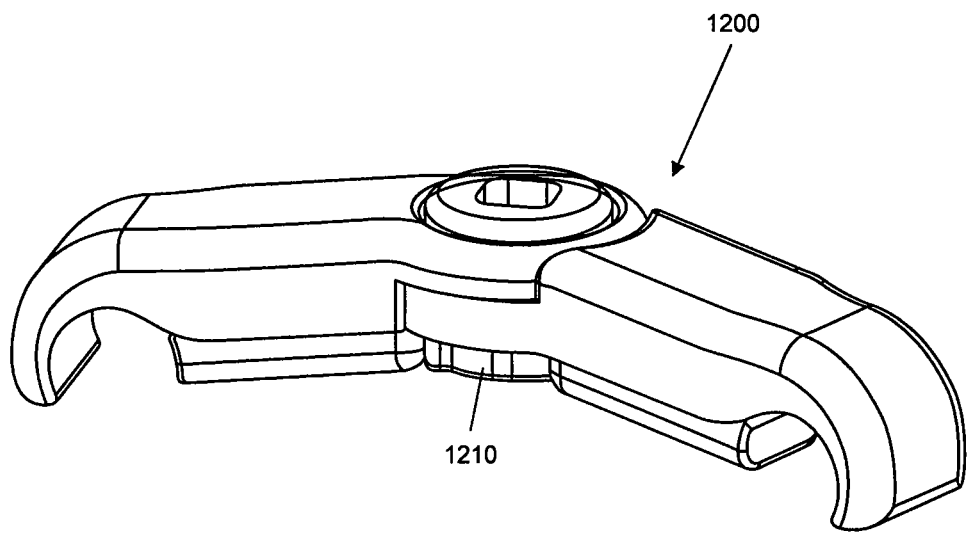
FIG. 12 is a perspective view of a fourth embodiment of a cross connector assembly.

FIG. 12 illustrates a perspective view of another alternative embodiment of a cross connector assembly 1200. In the illustrated embodiment, the cross connector assembly 1200 is substantially the same as the adjustable cross connector assembly 600 described above with reference to FIGS. 6-9, except that it includes a one-piece engagement member 1210 instead of upper and lower fasteners.

Figures 13A, 13B:
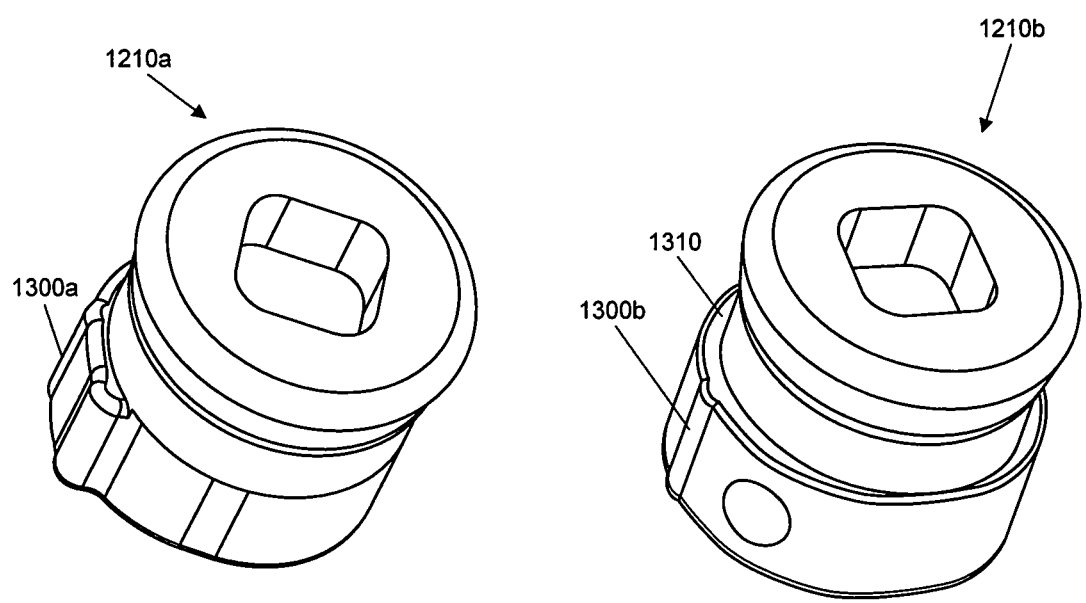
FIGS. 13A-B are perspective views of alternative embodiments of locking mechanisms for the fourth embodiment of the cross connector assembly.

FIGS. 13A and 13B illustrate perspective views of exemplary embodiments of a one-piece locking mechanism 1210a. In FIG. 13A, the one-piece locking mechanism 1210a is substantially circular except for a pair of projections 1300a. In the illustrated embodiment, the projections are rounded, but it should be understood that they may have any geometric profile. The projections are configured such that as the one-piece locking mechanism 1210a is rotated, the projections 1300a turn against a sliding members and biases it outwards. In the illustrated embodiment, the one-piece locking mechanism 1210a only employs a pair of projections 1300a on one side. In alternative embodiments (not shown), the one-piece locking mechanism 1210a may include two pairs of projections to engage both the first and second sliding members. It should be understood that the one-piece locking mechanism 1210a may be employed in any embodiment of a cross connector assembly, and its use is not limited to the cross connector assembly 1200 illustrated in FIG. 12.

In FIG. 13B, the one-piece locking mechanism 1210b includes a projection 1300b and further includes a cam-shaped surface 1310. In the illustrated embodiment, the projection is rounded, but it should be understood that it may have any geometric profile. The projection 1300b and the cam-shaped surface 1310 are configured such that as the one-piece locking mechanism 1210b is rotated, the projection 1300b and the cam-shaped surface 1310 turn against a sliding member and bias it outwards. In the illustrated embodiment, the one-piece locking mechanism 1210b only employs a projection 1300b on one side. In alternative embodiments (not shown), the one-piece locking mechanism 1210b may include two projections to engage both the first and second sliding members. It should be understood that the one-piece locking mechanism 1210b may be employed in any embodiment of a cross connector assembly, and its use is not limited to the cross connector assembly 1200 illustrated in FIG. 12.

Figure 14A:
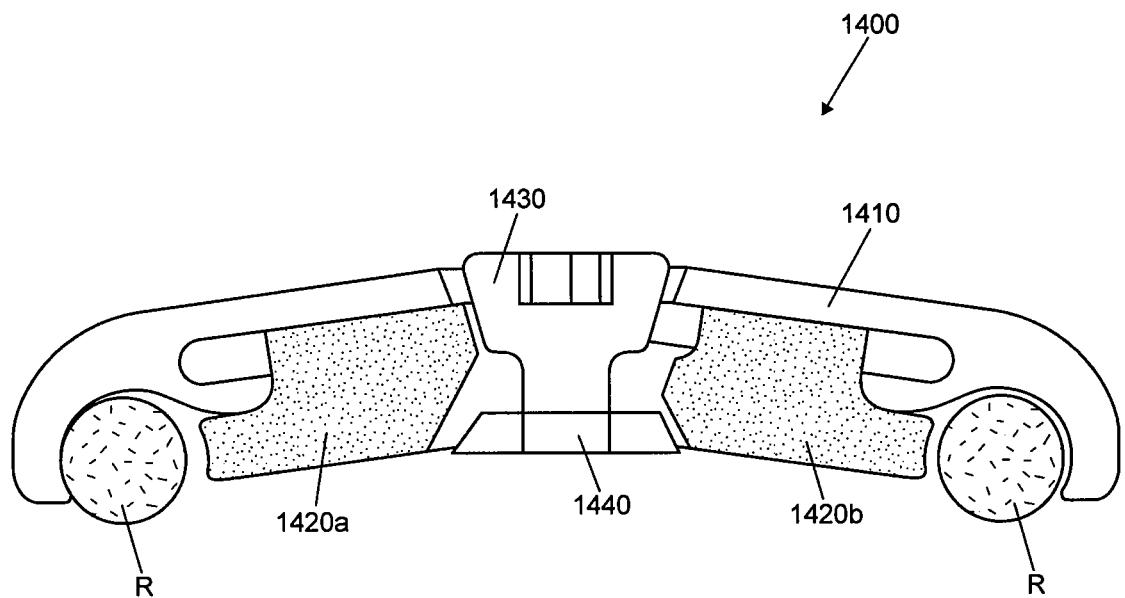
FIGS. 14A-B are front cross sections of a fifth embodiment of a cross connector assembly employing an alternative locking mechanism.
Figure 14B:
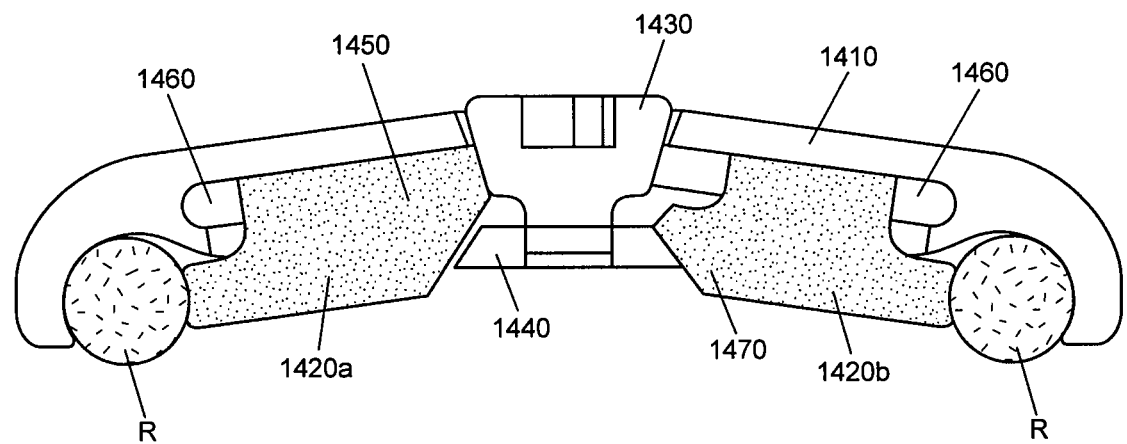

FIGS. 14A and 14B illustrate front cross-sections of an alternative embodiment of a cross connector assembly 1400. In the illustrated embodiment, the cross connector assembly 1400 includes a top elongated member 1410, first and second sliding members 1420a,b, and an engagement member including an upper fastener 1430 and a lower fastener 1440, similar to the corresponding components of the cross connector assembly 100 described above with reference to FIGS. 1-5, except for the differences that are detailed in the following paragraph. However, it should be understood that the cross connector assembly 1400 may employ any of the variations described in any of the embodiments of cross connector assemblies described herein.

In FIG. 14A, the cross-connector assembly 1400 is in an open position such that the hooked-shaped ends of the elongated top member 1410 may be placed over a pair of spinal rods R. After the cross-connector assembly 1400 is in place, a user may rotate the upper fastener 1430 by hand or with an appropriate tool. As the upper fastener 1430 is rotated, its threads mesh with the threaded aperture of the lower fastener 1440, causing the upper fastener 1430 to translate downwards and the lower fastener 1440 to translate upwards, as shown in FIG. 14B. As the upper fastener 1440 translates downwards, it pushes against an upper projection 1450 of the first sliding member 1420a, causing the first sliding member 1420a to slide outwards in a channel 1460 of the elongated top member 1410. Further, as the lower fastener 1440 moves upwards, an angled lower portion 1470 of the second sliding member 1420b slides along a groove of the lower fastener 1440, causing the second sliding member 1420b to slide outwards in a channel 1460 of the elongated top member 1410. The user may continue to rotate the upper fastener 1430 until the sliding members 1420,b contact the rods R and sufficient pressure is applied to lock the cross connector assembly 1400 in place.

Figure 15A:
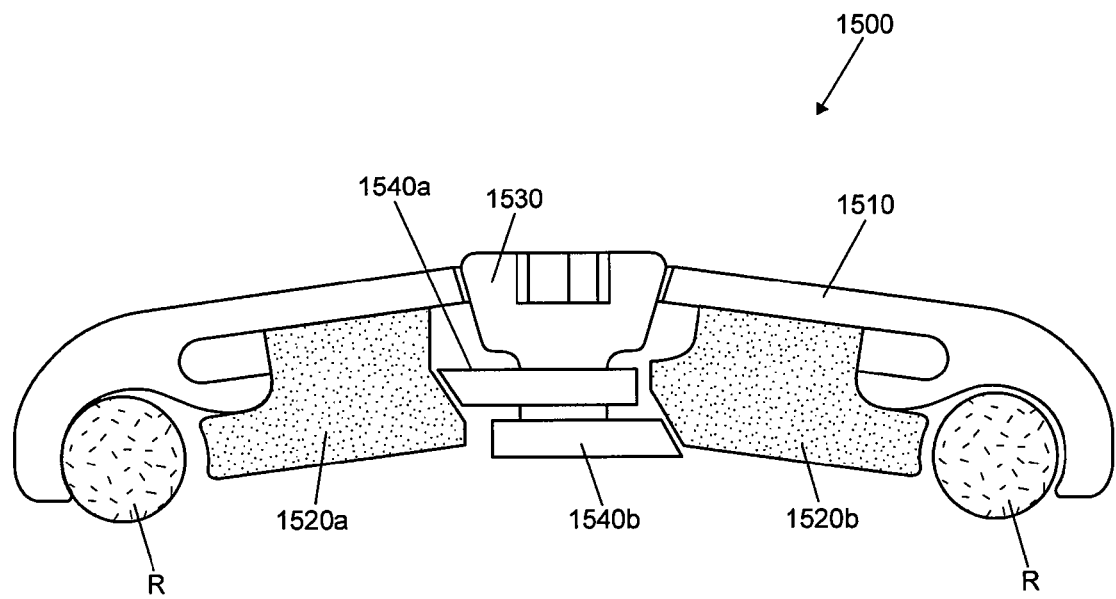
FIGS. 15A-B are front cross sections of a sixth embodiment of a cross connector assembly employing another alternative locking mechanism.
Figure 15B:
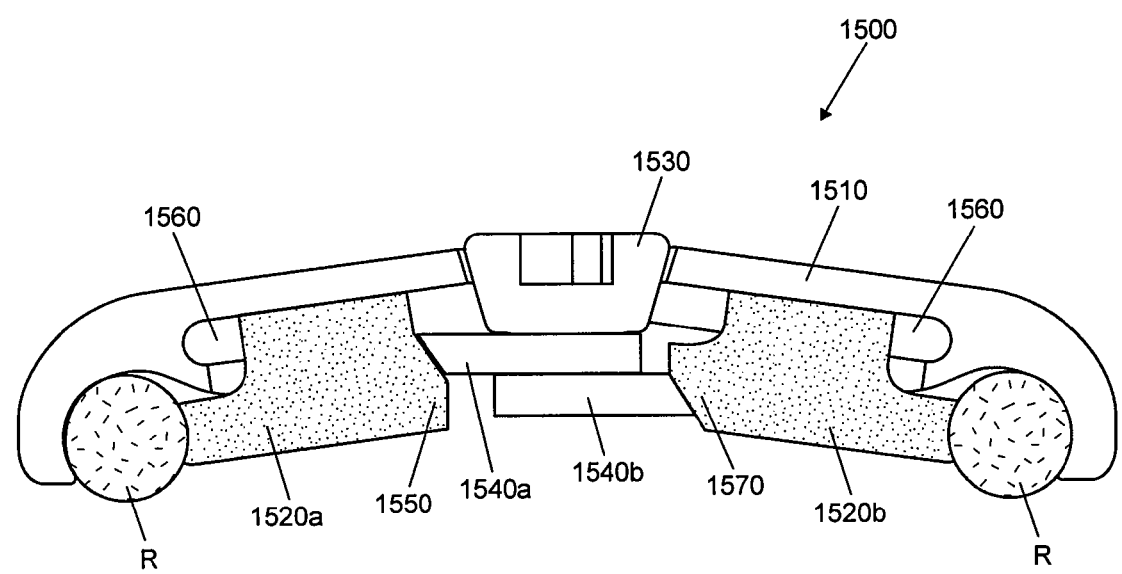

FIGS. 15A and 15B illustrate front cross-sections of an alternative embodiment of a cross connector assembly 1500. In the illustrated embodiment, the cross connector assembly 1500 includes a top elongated member 1510, first and second sliding members 1520a,b, and an engagement member including an upper fastener 1530 and a pair of lower fasteners 1540a,b, similar to the corresponding components of the cross connector assembly 100 described above with reference to FIGS. 1-5, except for the differences that are detailed in the following paragraph. However, it should be understood that the cross connector assembly 1500 may employ any of the variations described in any of the embodiments of cross connector assemblies described herein.

In FIG. 15A, the cross-connector assembly 1500 is in an open position such that the hooked-shaped ends of the elongated top member 1510 may be placed over a pair of spinal rods R. After the cross-connector assembly 1500 is in place, a user may rotate the upper fastener 1530 by hand or with an appropriate tool. As the upper fastener 1530 is rotated, its threads mesh with the threaded aperture of the pair of lower fasteners 1540a,b, causing the lower fasteners 1540a,b to translate upwards, as shown in FIG. 15B. As the lower fasteners 1540a,b move upwards, a first lower fastener 1540a pushes against a projection 1550 of the first sliding member 1520a, causing the first sliding member 1520a to slide outwards in a channel 1560 of the elongated top member 1510. At the same time, a second lower fastener 1540b pushes against a projection 1570 of the second sliding member 1520b, causing the second sliding member 1520b to slide outwards in a channel 1560 of the elongated top member 1510. The user may continue to rotate the upper fastener 1530 until the sliding members 1520,b contact the rods R and sufficient pressure is applied to lock the cross connector assembly 1500 in place.

Figure 16A:
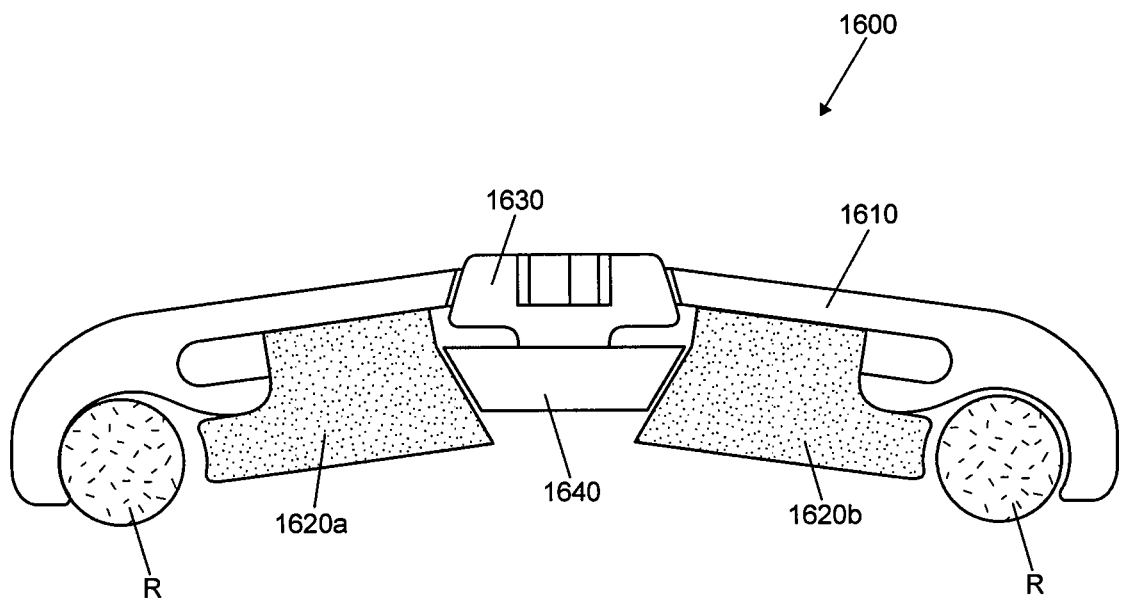
FIGS. 16A-B are front cross sections of a seventh embodiment of a cross connector assembly employing yet another alternative locking mechanism.
Figure 16B:
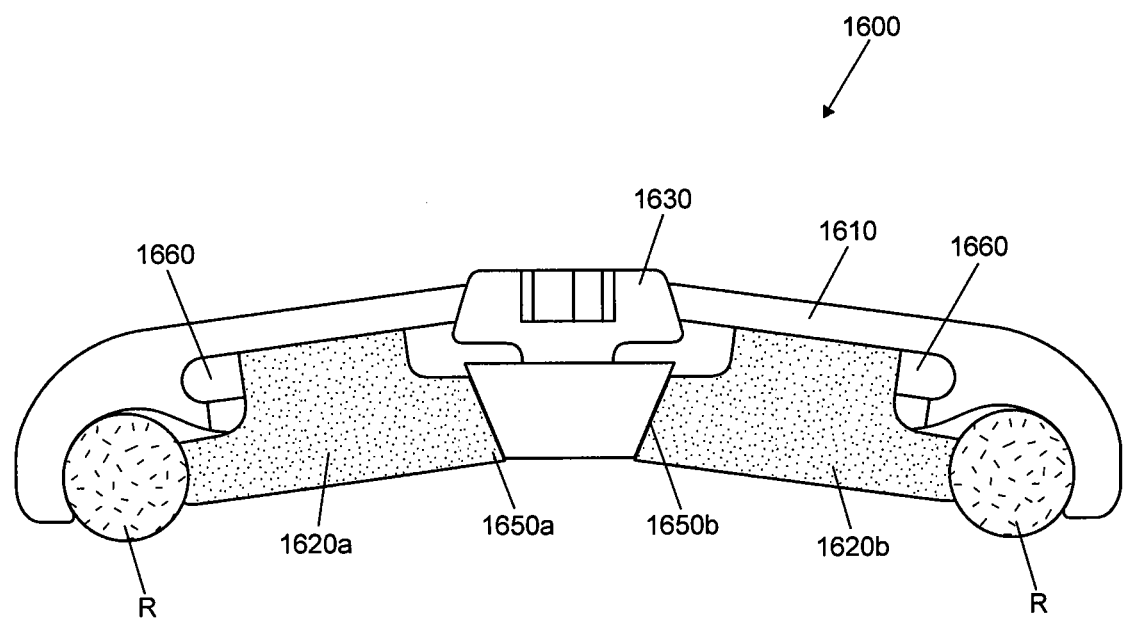

FIGS. 16A and 16B illustrate front cross-sections of an alternative embodiment of a cross connector assembly 1600. In the illustrated embodiment, the cross connector assembly 1600 includes a top elongated member 1610, first and second sliding members 1620a,b, and an engagement member including an upper fastener 1630 and a lower fastener 1640, similar to the corresponding components of the cross connector assembly 100 described above with reference to FIGS. 1-5, except for the differences that are detailed in the following paragraph. However, it should be understood that the cross connector assembly 1600 may employ any of the variations described in any of the embodiments of cross connector assemblies described herein.

In FIG. 16A, the cross-connector assembly 1600 is in an open position such that the hooked-shaped ends of the elongated top member 1610 may be placed over a pair of spinal rods R. After the cross-connector assembly 1600 is in place, a user may rotate the upper fastener 1630 by hand or with an appropriate tool. As the upper fastener 1630 is rotated, its threads mesh with the threaded aperture of the lower fastener 1640, causing the lower fastener 1640 to translate downwards, as shown in FIG. 16B. As the lower fastener 1640 moves downwards, it pushes against projections 1650a,b of the first and second sliding members 1620a,b, causing the first and second sliding members 1620a,b to slide outwards in a channel 1660 of the elongated top member 1610. The user may continue to rotate the upper fastener 1630 until the sliding members 1620,b contact the rods R and sufficient pressure is applied to lock the cross connector assembly 1600 in place.

It should be understood that the cross connector assembly of the present application is not limited to the above described embodiments. Other variations, such as a cross connector assembly with telescoping arms may be employed without departing from the scope of this patent.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. For example, one of the above described embodiments may further employ telescoping arms. Therefore, the application, in its broader aspects, is not limited to the specific details, the representative apparatus, and illustrative examples shown and described. Accordingly, departures may be made from such details without departing from the spirit or scope of the applicant's general inventive concept.

What is claimed is:

1. A cross connector assembly comprising:
at least one elongated top member having a pair of hooked-shaped ends, the at least one elongated top member including a first elongated top member pivotally connected to a second elongated top member;
a pair of elongated sliding members extending in the same direction as the top member, each one of the pair of sliding members configured to only slide linearly along the at least one elongated top member toward and away from at least one hooked shaped end;
an upper fastener; and
at least one lower fastener engaged with the upper fastener between the pair of hooked-shaped ends and configured to engage at least one of the sliding members, biasing the at least one sliding member from a first position to a second position, the upper fastener and the at least one lower fastener being axially movable relative to each other.

2. The cross connector assembly of claim 1, wherein each of the first and second elongated top members further includes a pivotal end.

3. The cross connector assembly of claim 1, wherein the at least one elongated top member includes an oblong aperture configured to receive the upper fastener.

4. The cross connector assembly of claim 1, wherein the at least one lower fastener is configured to translate along the upper fastener upon rotation of the upper fastener.

5. A cross connector for a spinal fixation assembly, the cross connector comprising:
an upper body having at least two elongated members, including a first elongated member having a first rod receiving portion and a second elongated member having a second rod receiving portion, wherein the first elongated member is pivotally connected to the second elongated member;
at least two sliding members, including a first sliding member configured to slideably engage the first elongated member and a second sliding member configured to slideably engage the second elongated member; and
an engagement member configured to engage the at least two sliding members and bias them towards the first and second rod receiving portions, the engagement member being configured to prevent pivotal movement between the first and second elongated members.

6. The cross connector of claim 5, wherein the engagement member includes an upper fastener and at least one lower fastener.

7. The cross connector of claim 5, wherein the engagement member includes a cam.

8. The cross connector of claim 5, wherein the first elongated member includes a first pivoting finger and the second locking member includes a second pivoting finger.

9. The cross connector of claim 5, wherein the first elongated member is pivotally connected to the second elongated member via a pivotal connection having a plurality of detent positions.

10. A cross connector for a spinal fixation assembly, the cross connector comprising:

an upper body having at least two elongated members, including a first elongated member having a first rod receiving portion and a second elongated member having a second rod receiving portion, wherein the first elongated member is pivotally connected to the second elongated member;

at least two sliding members, including a first sliding member configured to slideably engage the first elongated member and a second sliding member configured to slideably engage the second elongated member;

an engagement member configured to engage the at least two sliding members and bias them towards the first and second rod receiving portions; and a stop configured to define a range through which the first elongated member pivots with respect to the second elongated member.

11. The cross connector of claim 10, wherein the range is between about −45° to about 45°.

12. A cross connector assembly comprising:

an upper member including a first elongated member having a first pivoting finger and a second elongated member having a second pivoting finger, wherein the first elongated member is pivotally connected to the second elongated member, the first pivoting finger being pivotable about an axis extending transverse to the length of the first elongated member, the second pivoting finger being pivotable about an axis extending transverse to a length of the second elongated member;

a first sliding member configured to slideably engage the first elongated member and a second sliding member configured to slideably engage the second elongated member; and means for biasing the sliding members.

13. The cross connector assembly of claim 12, wherein the upper member includes an oblong recess configured to receive the means for biasing the sliding members.

14. The cross connector of claim 12, further including a stop configured to define a range through which the first elongated member pivots with respect to the second elongated member.

15. The cross connector assembly of claim 14, wherein the range is between about −45° to about 45°.

16. The cross connector assembly of claim 12, wherein the first elongated member is pivotally connected to the second elongated member via a pivotal connection having a plurality of detent positions.

17. The cross connector assembly of claim 12, wherein the upper body further includes at least one channel configured to receive the first and second sliding members.

* * * * *